(12) United States Patent
Vidal et al.

(10) Patent No.: US 7,192,452 B2
(45) Date of Patent: Mar. 20, 2007

(54) PYRAZOLO-TRIAZOLES AND USE OF SAID COMPOUNDS FOR DYEING KERATINOUS FIBRES

(75) Inventors: Laurent Vidal, Paris (FR); Sylvie Genard, Nogent sur Marne (FR)

(73) Assignee: L'Oreal S.A., Paris (FR)

( * ) Notice: Subject to any disclaimer, the term of this patent is extended or adjusted under 35 U.S.C. 154(b) by 200 days.

(21) Appl. No.: 10/467,818

(22) PCT Filed: Feb. 13, 2002

(86) PCT No.: PCT/FR02/00552

§ 371 (c)(1),
(2), (4) Date: Nov. 20, 2003

(87) PCT Pub. No.: WO02/064596

PCT Pub. Date: Aug. 22, 2002

(65) Prior Publication Data

US 2004/0088801 A1 May 13, 2004

(30) Foreign Application Priority Data

Feb. 14, 2001 (FR) ................ 01 02001

(51) Int. Cl.
*A61K 7/13* (2006.01)
(52) U.S. Cl. .............. 8/405; 8/406; 8/408; 8/409; 8/411; 8/412; 8/421; 8/435; 548/300
(58) Field of Classification Search .......... 8/405, 8/406, 408, 409, 411, 412, 421, 435, 573; 548/300
See application file for complete search history.

(56) References Cited

U.S. PATENT DOCUMENTS

| | | | |
|---|---|---|---|
| 4,003,699 A | 1/1977 | Rose et al. ............ 8/10.2 |
| 4,823,985 A | 4/1989 | Grollier et al. ............ 222/1 |
| 5,061,289 A | 10/1991 | Clausen et al. ............ 8/405 |
| 5,380,340 A | 1/1995 | Neunhoeffer et al. ........ 8/409 |
| 5,766,576 A | 6/1998 | Löwe et al. ............ 424/62 |
| 6,099,592 A | 8/2000 | Vidal et al. ............ 8/409 |
| 6,099,593 A | 8/2000 | Terranova et al. ........... 8/409 |
| 6,231,623 B1 * | 5/2001 | Vidal et al. ............ 8/409 |
| 2002/0007520 A1 | 1/2002 | Vidal et al. ............ 8/405 |

FOREIGN PATENT DOCUMENTS

| DE | 23 59 399 | 6/1975 |
|---|---|---|
| DE | 38 43 892 | 6/1990 |
| DE | 41 33 957 | 4/1993 |
| DE | 195 43 988 | 5/1997 |
| EP | 0 770 375 | 5/1997 |
| EP | 0 923 929 | 6/1999 |
| EP | 1 040 818 | 10/2000 |
| FR | 2 586 913 | 3/1987 |
| FR | 2 733 749 | 11/1996 |
| FR | 2 746 303 | 9/1997 |
| FR | 2 750 048 | 12/1997 |
| GB | 1 026 978 | 4/1966 |
| GB | 1 153 196 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 96/15765 | 5/1996 |
| WO | WO 97/35551 | * 10/1997 |

OTHER PUBLICATIONS

English language Derwent Abstract of EP 0 770 375, May 2, 1997.
English language Derwent Abstract of EP 1 040 818, Oct. 4, 2000.
English language Derwent Abstract of FR 2 746 303, Sep. 26, 1997.
English language Derwent Abstract of JP 2-19576, Jan. 23, 1990.
English language Derwent Abstract of JP 5-163124, Jan. 29, 1993.
H. Wilde et al., "Synthese von 4 H-Pyrazolo[1,5-a]benzimidazolen[1]," Journal f. prakt. Chemie., Band 326, Heft 5, 1984, S. 829-836.
Mohamed Helmy Elnagdi et al., "Routes for the Synthesis of 3,5-Diaminopyrazoles, 2-Aminopyrazolo[1,5-a]pyrimidines and 5-Aminopyrazolo[1,5-a]pyrimidines," Journal f. prakt. Chemie., Band 320, Heft 4, 1978, S. 533-538.
Joseph Bailey, "Synthesis of 1*H*-Pyrazolo[3,2-c]-s-Triazoles and Derived Azamethine Dyes," Journal of The Chemical Society, Perkin Transactions 1, 1977, pp. 2047-2056.

* cited by examiner

*Primary Examiner*—Eisa Elhilo
(74) *Attorney, Agent, or Firm*—Finnegan, Henderson, Farabow, Garrett & Dunner L.L.P.

(57) ABSTRACT

The subject of the invention is novel pyrazolo[3,2-c]-1,2,4-triazoles of formula (I) which are useful for the oxidation dyeing of keratinous fibers, in particular human hair, the compositions containing these compounds and the dyeing method using them.

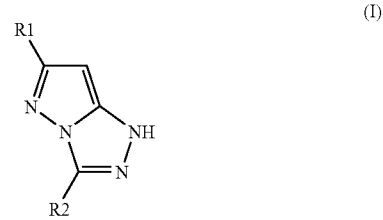

(I)

in which
R1 represents a hydroxyl group or a C1–C4 alkyl group substituted with at least one hydroxyl radical, and R2 represents an aryl group which may be substituted with at least one radical chosen from the group consisting of halogen, nitro, cyano, alkyl, hydroxyl, alkoxy, amino, alkylamino, dialkylamino, acylamino, sulfonamido, alkylthio, alkoxycarbonyl, carboxy and sulfo radicals.

21 Claims, No Drawings

PYRAZOLO-TRIAZOLES AND USE OF SAID COMPOUNDS FOR DYEING KERATINOUS FIBRES

The subject of the invention is novel pyrazolo[3,2-c]-1,2,4-triazoles which are useful for the oxidation dyeing of keratinous fibers, in particular human hair, the compositions containing these compounds and the dyeing method using them.

It is known to dye keratinous fibers, and in particular human hair, with dyeing compositions containing oxidation dye precursors, generally called oxidation bases, such as ortho- or para-phenylenediamines, ortho- or para-aminophenols and heterocyclic compounds. These oxidation bases are colorles's or weakly colored compounds which, combined with oxidizing products, can give rise, through a process of oxidative condensation, to colored compounds.

It is also known that it is possible to vary the shades obtained with these oxidation bases by combining them with couplers or color modifiers the latter being chosen in particular from aromatic meta-diamines, meta-aminophenols, meta-diphenols and certain heterocyclic compounds such as indole compounds.

The variety of molecules used in oxidation bases and couplers allows a rich palette of colors to be obtained.

The so-called "permanent" color obtained using these oxidation dyes must moreover satisfy a number of requirements. Thus, it must be without drawbacks from the toxicological point of view, it must make it possible to obtain shades in the desired intensity and exhibit good resistance toward external agents such as light, adverse weather conditions, washing, permanent waving, perspiration and rubbing.

The dyes must also make it possible to cover gray hair and must finally be the least selective possible, that is to say make it possible to obtain the smallest possible differences in color right along the same keratinous fiber, which is generally differently sensitized (i.e. damaged) between its tip and its root.

It is already known to use pyrazoloazole compounds as couplers for dyeing keratinous fibers. For example, patent application FR 2 746 306 describes compositions for dyeing keratinous fibers containing such couplers. These compositions are nevertheless not completely satisfactory, in particular they are not completely satisfactory from the point of view of the purity of the shades.

The aim of the present invention is to provide novel dyeing compositions not having the drawbacks of those of the prior art. In particular, the aim of the present invention is to provide compositions for the oxidation dyeing of keratinous fibers which have powerful dyes, which are scarcely selective and are particularly resistant, which are capable of generating intense colorations in a variety of shades, and which have a coloration which scarcely varies during a deferred application.

This aim is achieved with the present invention whose subject is a novel pyrazolo[3,2-c]-1,2,4-triazole of formula (I) or one of its addition salts with an acid or a base:

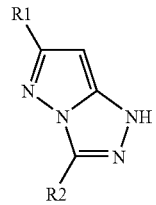

in which
R1 represents a hydroxyl group or a C1–C4 alkyl group substituted with at least one hydroxyl radical, and R2 represents an aryl, for example phenyl or naphthyl, group which may be substituted with at least one radical chosen from the group consisting of halogen, nitro, cyano, alkyl, hydroxyl, alkoxy, amino, alkylamino, dialkylamino, acylamino, sulfonamido, alkylthio, alkoxycarbonyl, carboxy and sulfo radicals.

According to a particular embodiment, R1 is a C1–C4 alkyl group which are substituted with 1 to 3 hydroxyl radicals and R2 is a phenyl group which may be substituted with 1 to 3 radicals, preferably 1 to 2 radicals.

R1 is for example chosen from hydroxymethyl, 2-hydroxyethyl, 3-hydroxypropyl, 1-hydroxyethyl, 1-hydroxypropyl, 1-methyl-2-hydroxyethyl, 1,2-dihydroxyethyl, 2,3-dihydroxypropyl, 1,3-dihydroxypropyl, 1,3-dihydroxybutyl, 2,4-dihydroxybutyl, 1,2,3-trihydroxypropyl, 1,2,3-trihydroxybutyl. Preferably, R1 is chosen from hydroxymethyl, 1-hydroxyethyl, 2-hydroxyethyl, 1-methyl-2-hydroxyethyl, 1,2-dihydroxyethyl.

R2 is for example chosen from a phenyl group or a phenyl group substituted with radicals chosen from halogen, C1–C4 alkyl, C1–C4 alkoxy, hydroxyl, carboxyl, C1–C4 alkylthio, amino, C1–C4 alkylamino, C1–C4 dialkylamino and methylenedioxy radicals. Preferably, R2 is chosen from phenyl, toluyl, 2-, 3- or 4-chlorophenyl, 3- or 4-hydroxyphenyl, 3- or 4-aminophenyl and 3- or 4-methoxyphenyl. According to a particularly preferred embodiment, the groups R2 are chosen from phenyl, toluyl, 3- or 4-hydroxyphenyl and 3- or 4-aminophenyl.

In the above definitions, the alkyl radicals or groups are linear or branched and comprise, unless otherwise stated, from 1 to 10 carbon atoms, preferably 1 to 6 carbon atoms.

Among the pyrazolo[3,2-c]-1,2,4-triazoles of formula (I), there may be mentioned in particular the following compounds or their addition salts with an acid or a base:
6-hydroxymethyl-3-phenylpyrazolo[3,2-c]-1,2,4-triazole
6-hydroxymethyl-3-(p-toluyl)pyrazolo[3,2-c]-1,2,4-triazole
6-hydroxymethyl-3-(o-toluyl)pyrazolo[3,2-c]-1,2,4-triazole
6-hydroxymethyl-3-(m-toluyl)pyrazolo[3,2-c]-1,2,4-triazole
6-hydroxymethyl-3-(3-hydroxyphenyl)pyrazolo[3,2-c]-1,2,4-triazole
6-hydroxymethyl-3-(4-hydroxyphenyl)pyrazolo[3,2-c]-1,2,4-triazole
6-hydroxymethyl-3-(3-aminophenyl)pyrazolo[3,2-c]-1,2,4-triazole
6-hydroxymethyl-3-(4-aminophenyl)pyrazolo[3,2-c]-1,2,4-triazole
6-(2-hydroxyethyl)-3-phenylpyrazolo[3,2-c]-1,2,4-triazole
6-(2-hydroxyethyl)-3-(p-toluyl)pyrazolo[3,2-c]-1,2,4-triazole
6-(2-hydroxyethyl)-3-(o-toluyl)pyrazolo[3,2-c]-1,2,4-triazole 6-(2-hydroxyethyl)-3-(m-toluyl)pyrazolo[3,2-c]-1,2,4-triazole
6-(2-hydroxyethyl)-3-(3-hydroxyphenyl)pyrazolo[3,2-c]-1,2,4-triazole
6-(2-hydroxyethyl)-3-(4-hydroxyphenyl)pyrazolo[3,2-c]-1,2,4-triazole
6-(2-hydroxyethyl)-3-(3-aminophenyl)pyrazolo[3,2-c]-1,2,4-triazole
6-(2-hydroxyethyl)-3-(4-aminophenyl)pyrazolo[3,2-c]-1,2,4-triazole
6-(1-hydroxyethyl)-3-phenylpyrazolo[3,2-c]-1,2,4-triazole
6-(1-hydroxyethyl)-3-(p-toluyl)pyrazolo[3,2-c]-1,2,4-triazole
6-(1-hydroxyethyl)-3-(o-toluyl)pyrazolo[3,2-c]-1,2,4-triazole
6-(1-hydroxyethyl)-3-(m-toluyl)pyrazolo[3,2-c]-1,2,4-triazole
6-(1-hydroxyethyl)-3-(3-hydroxyphenyl)pyrazolo[3,2-c]-1,2,4-triazole
6-(1-hydroxyethyl)-3-(4-hydroxyphenyl)pyrazolo[3,2-c]-1,2,4-triazole
6-(1-hydroxyethyl)-3-(3-aminophenyl)pyrazolo[3,2-c]-1,2,4-triazole
6-(1-hydroxyethyl)-3-(4-aminophenyl)pyrazolo[3,2-c]-1,2,4-triazole.

Preferably, the pyrazolo[3,2-c]-1,2,4-triazoles of formula (I) are chosen from the following compounds or their addition salts with an acid or a base:
6-hydroxymethyl-3-phenylpyrazolo[3,2-c]-1,2,4-triazole
6-hydroxymethyl-3-(p-toluyl)pyrazolo[3,2-c]-1,2,4-triazole
6-hydroxymethyl-3-(o-toluyl)pyrazolo[3,2-c]-1,2,4-triazole
6-hydroxymethyl-3-(m-toluyl)pyrazolo[3,2-c]-1,2,4-triazole
6-hydroxymethyl-3-(3-hydroxyphenyl)pyrazolo[3,2-c]-1,2,4-triazole
6-hydroxymethyl-3-(4-hydroxyphenyl)pyrazolo[3,2-c]-1,2,4-triazole
6-hydroxymethyl-3-(3-aminophenyl)pyrazolo[3,2-c]-1,2,4-triazole
6-hydroxymethyl-3-(4-aminophenyl)pyrazolo[3,2-c]-1,2,4-triazole.

The compounds of the present invention may be obtained from the methods of preparation described for example in patent application FR 2 746 306, and in the following publications: Chem. Ber. 32, 797 (1899), Chem. Ber. 89, 2550, (1956), J. Chem. Soc. Perkin trans I,2047, (1977), J. Prakt. Chem., 320, 533, (1978), J. fur Chem., 326(5), 829, (1984).

The subject of the invention is also a composition for dyeing keratinous fibers, and in particular human keratinous fibers such as hair, comprising, in an appropriate dyeing medium, at least one pyrazolotriazole coupler of formula (I) or one of these addition salts with an acid or a base as defined above and at least one oxidation base.

The oxidation base is chosen from the oxidation bases conventionally used in oxidation dyeing, for example para-phenylenediamines, bisphenylalkylenediamines, para-aminophenols, ortho-aminophenols and heterocyclic bases, and their addition salts with an acid.

Among the para-phenylenediamines, there may be mentioned by way of example para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the para-phenylenediamines mentioned above, there are particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

Among the bisphenylalkylenediamines, there may be mentioned by way of example N,N'-bis(β-phydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and their addition salts with an acid.

Among the para-aminophenols, there may be mentioned by way of example para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols, there may be mentioned by way of example 2-aminophenol, 2-amino-5-methylphenol, 2-amino-6-methylphenol, 5-acetamido-2-aminophenol, and their addition salts with an acid.

Among the heterocyclic bases, there may be mentioned by way of example pyridine derivatives, pyrimidine derivatives and pyrazole derivatives.

Among the pyridine derivatives, there may be mentioned the compounds described for example in Patent GB 1,026,978 and GB 1,153,196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their acid addition salts with an acid.

Among the pyrimidine derivatives, there may be mentioned the compounds described for example in Patents DE 2,359,399; JP 88-169,571; JP 05,163,124; EP 0,770,375 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in Patent Application FR-A-2,750,048 and among which there may be mentioned pyrazolo[1,5-a]pyrimidine-3,7-diamine;

2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine and their addition salts with an acid and their tautomeric forms, when a tautomeric equilibrium exists.

Among the pyrazole derivatives, there may be mentioned the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts with an acid.

In the composition of the present invention, the pyrazolotriazole coupler(s) are present in a quantity preferably of between 0.001 and 10% by weight approximately of the total weight of the dyeing composition and still more preferably from 0.005 to 6%, and the oxidation base(s) are present in a quantity preferably of between 0.001 to 10% by weight approximately of the total weight of the dyeing composition, and still more preferably from 0.005 to 6%.

The composition according to the invention may contain, in addition to the pyrazolotriazole coupler of formula (I), one or more additional couplers which are conventionally used for dyeing keratinous fibers. Among these couplers, there may be mentioned in particular meta-phenylenediamines, meta-aminophenols, meta-diphenols and heterocyclic couplers.

By way of example, there may be mentioned 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-napthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene and their addition salts.

When they are present, the additional coupler(s) preferably represent from 0.001 to 10% by weight approximately of the total weight of the dyeing composition and still more preferably from 0.005 to 6%.

In general, the addition salts with an acid which can be used in the context of the dyeing compositions of the invention for the oxidation bases and the couplers are chosen in particular from hydrochlorides, hydrobromides, sulfates, citrates, succinates, tartrates, lactates, tosylates, benzenesulfonates, phosphates and acetates. The addition salts with a base which can be used in the context of the invention are for example chosen the addition salts with sodium hydroxide, potassium hydroxide, aqueous ammonia, amines or alkanolamines.

The dyeing composition in accordance with the invention may additionally contain one or more direct dyes which may be chosen in particular from nitro dyes of the benzene series, cationic direct dyes, azo direct dyes and methine direct dyes.

The appropriate dyeing medium, also called dye carrier, generally consists of water or of a mixture of water and at least one organic solvent for solubilizing the compounds which might not be sufficiently soluble in water. By way of organic solvent, there may be mentioned for example $C_1$–$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, and mixtures thereof.

The solvents may be present in proportions preferably of between 1 and 40% by weight approximately relative to the total weight of the dyeing composition, and still more preferably between 5 and 30% by weight approximately.

The dyeing composition in accordance with the invention may also comprise various adjuvants which are conventionally used in hair dyeing compositions, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, associative or otherwise, antioxidants, penetrating agents, sequestering agents, perfumes, buffers, dispersing agents, conditioning agents such as for example modified or unmodified, volatile or nonvolatile silicones, film-forming agents, ceramides, preservatives, opacifying agents.

The above adjuvants are generally present in a quantity, for each of them, of between 0.01 and 20% by weight relative to the weight of the composition.

Of course, persons skilled in the art will be careful to choose this or these optional additional compounds such that the advantageous properties which are intrinsically attached to the oxidation dyeing composition in accordance with the invention are not, or not substantially, impaired by the addition(s) envisaged.

The pH of the dyeing composition in accordance with the invention is generally between 3 and 12 approximately, and preferably between 5 and 11 approximately. It may be adjusted to the desired value by means of acidifying or alkalinizing agents customarily used in dyeing keratinous fibers or alternatively with the aid of conventional buffer systems.

Among the acidifying agents, there may be mentioned, by way of example, inorganic or organic acids such as hydrochloric acid, orthophosphoric acid, sulfuric acid, carboxylic acids such as acetic acid, tartaric acid, citric acid, lactic acid, and sulfonic acids.

Among the alkalinizing agents, there may be mentioned, by way of example, aqueous ammonia, alkali metal carbonates, alkanolamines such as mono-, di- and triethanolamines and their derivatives, sodium or potassium hydroxides and the compounds having the following formula (III):

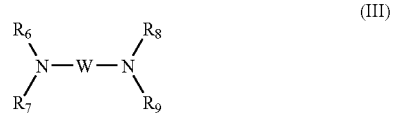

in which W is a propylene residue which is optionally substituted with a hydroxyl group or a $C_1$–$C_4$ alkyl radical; $R_6$, $R_7$, $R_8$ and $R_9$, which are identical or different, represent a hydrogen atom, a $C_1$–$C_4$ alkyl or $C_1$–$C_4$ hydroxyalkyl radical.

The dyeing composition according to the invention may be provided in various forms, such as in the form of liquids, creams, gels, or in any other form appropriate for dyeing keratinous fibers, and in particular human hair.

The subject of the invention is also a method for dyeing keratinous fibers, and in particular human keratinous fibers such as hair, using the dyeing composition as defined above.

According to this method, the composition according to the present invention as defined above is applied to the fibers, the color being developed with the aid of an oxidizing agent. The color may be developed at acidic, neutral or alkaline pH, and the oxidizing agent may be added to the composition of the invention just at the time of use or it may be used from an oxidizing composition containing it, which is applied simultaneously with or sequentially to the composition of the invention.

According to a particular embodiment, the composition according to the present invention is mixed, preferably at the time of use, with a composition containing, in an appropriate dyeing medium, at least one oxidizing agent, this oxidizing agent being present in a sufficient quantity to develop a coloration. The mixture obtained is then applied to the keratinous fibers. After a leave-in time of 3 to 50 minutes approximately, preferably 5 to 30 minutes approximately, the keratinous fibers are rinsed, washed with shampoo, rinsed again and then dried.

The oxidizing agents conventionally used for the oxidation dyeing of keratinous fibers are for example hydrogen peroxide, urea peroxide, alkali metal bromates, persalts such as perborates and persulfates, peracids and oxidase enzymes among which there may be mentioned peroxidases, oxidoreductases containing two electrons such as uricases and oxygenases containing 4 electrons such as laccases. Hydrogen peroxide is particularly preferred.

The oxidizing composition may also contain various adjuvants conventionally used in hair-dyeing compositions and as defined above.

The pH of the oxidizing composition containing the oxidizing agent is such that after mixing with the dyeing composition, the pH of the resulting composition applied to the keratinous fibers preferably varies between 3 and 12 approximately, and still more preferably between 5 and 11. It may be adjusted to the desired value by means of acidifying or alkalinizing agents customarily used in dyeing keratinous fibers and as defined above.

The composition which is finally applied to the keratinous fibers may be provided in various forms, such as in the form of liquids, creams, gels or in any other form appropriate for dyeing keratinous fibers, and in particular human hair.

Another subject of the invention is a multicompartment device or dyeing "kit" in which a first compartment contains the dyeing composition defined above and a second compartment contains the oxidizing composition. This device may be equipped with a means which makes it possible to deliver the desired mixture to the hair, such as the devices described in patent FR-2-586 913 in the name of the applicant.

The subject of the present invention is finally a method for synthesizing a compound of formula (II) from a compound of formula (III)

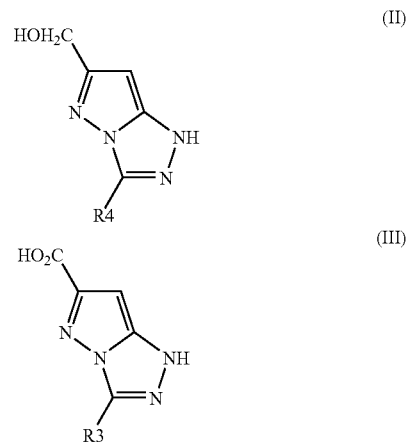

in which formulae R3 and R4, which are identical or different, represent an aryl, for example phenyl or naphthyl, group which may be substituted with at least one radical chosen from the group consisting of halogen, alkyl, hydroxyl, alkoxy, amino, alkylamino, dialkylamino and alkylthio radicals, the method comprising a step of reducing the carboxyl functional group to an alcohol functional group.

R3 and R4 are for example chosen from a phenyl group or a phenyl group substituted with one or two groups chosen from halogen, C1–C2 alkyl, C1–C2 alkoxy, hydroxyl, C1–C2 alkylthio, amino, C1–C2 alkylamino, C1–C2 dialkylamino and methylenedioxy radicals. Preferably, R3 and R4 are chosen from phenyl, toluyl, 2-, 3- or 4-chlorophenyl, 3- or 4-hydroxyphenyl, 3- or 4-aminophenyl, 3- or 4-methoxyphenyl. According to a particularly preferred embodiment, the groups R3 and R4 are chosen from phenyl, toluyl, 3- or 4-hydroxyphenyl, 3- or 4-aminophenyl.

The method of synthesis is carried out in one or more stages according to the nature of the substituent R3.

When the groups R3 and R4 are different, the method comprises one or more additional stages aimed at converting R3 to R4. Furthermore, the compound (III) may be converted to an ester before the reduction stage. Such a modification may be useful for increasing the solubility of the compound (III) and facilitating the reduction.

Thus, when R3 and R4 are identical, the reduction of the carboxylic acid functional group at the 6-position to an alcohol functional group may be carried out in a direct manner in a single step with the customary reducing agents such as metal hydrides, for example LiAlH$_4$, DIBAL, NaAlEt$_2$H$_2$, LiAlH(OMe)$_3$ or borane, these reagents being introduced at least in a stoichiometric quantity. Solvents used are for example THF, ethers or DME. This route of synthesis is represented by scheme 1 below.

Scheme 1:

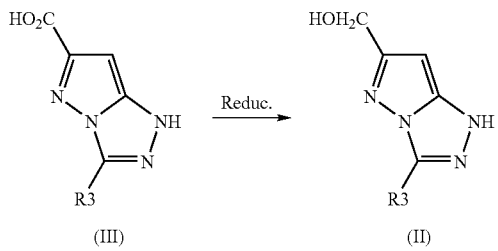

According to the nature of the substituent R3, the solubility of the compound (III) may be low in aprotic dipolar solvents. It may be advantageous in this case to convert, in a first stage, the carboxylic acid functional group of the compound (III) to a methyl or ethyl ester functional group in order to increase the solubility of the compound (III), and then, in a second stage, to reduce the ester functional group with conventional reducing agents in an aprotic dipolar solvent in order to obtain the corresponding compound (II). This embodiment is represented in scheme 2 below. The preparation of the methyl, respectively ethyl, ester is carried out by the customary methods such as for example by reaction of the carboxylic acid functional group in methanol, respectively in ethanol, in an acid medium.

Scheme 2:

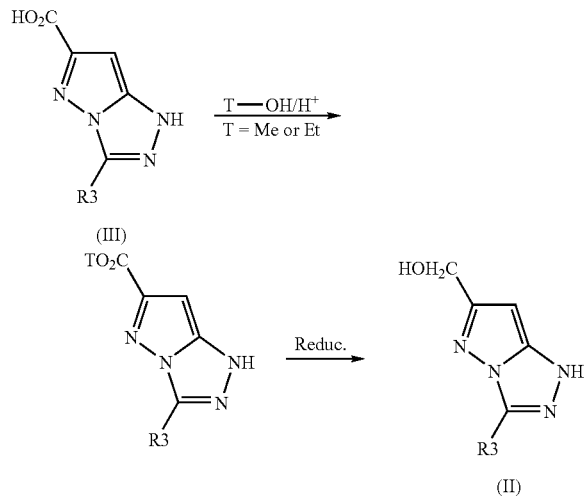

When R3 and R4 are different, the chemical modifications of the substituent R3 may be carried out either on the compound (II) or on the compound (III) according to the nature of the modifications to be made or according to their ease of implementation on either of the compounds. In this case, the preparation of the compound (II) from the compound (III) may be carried out by any of the schemes 3 to 6 below Scheme 3:

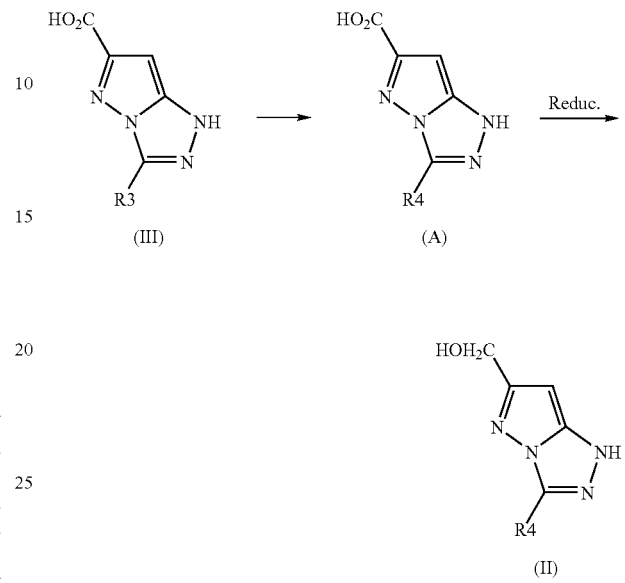

Scheme 4:

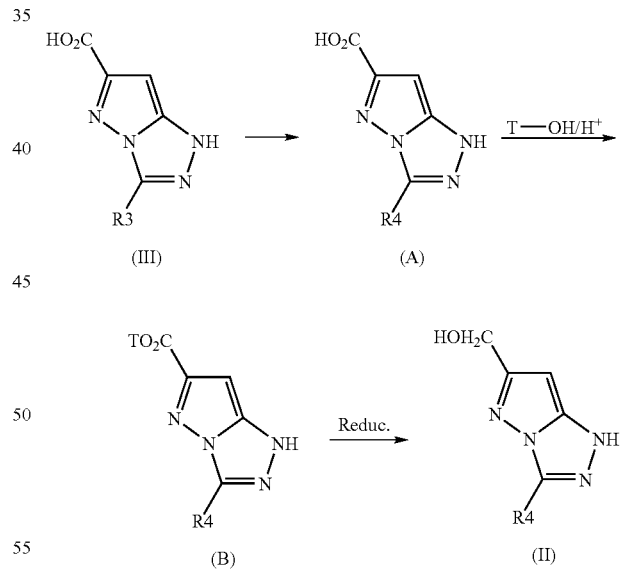

Scheme 5:

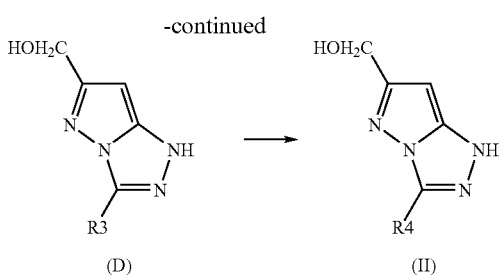

(D) → (II)

Scheme 6:

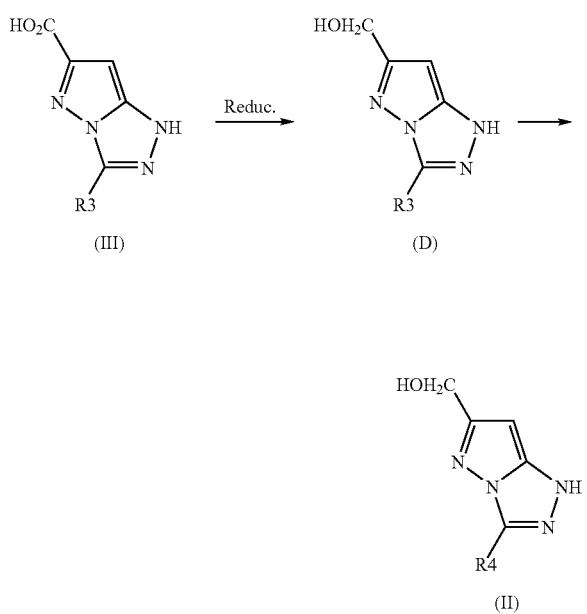

(III) —Reduc.→ (D) → (II)

According to scheme 3, the compound (III) is converted to compound A under the operating conditions necessary for converting R3 to R4. The compound A is then reduced under the operating conditions already described for obtaining compound (II).

According to scheme 4, the carboxylic acid functional group of the compound (III) is converted to a methyl or ethyl ester in order to form the compound B according to the methods described above. The compound B is then reduced under the operating conditions already described for obtaining compound (II).

A particular embodiment is described in scheme 5, according to which the methyl or ethyl ester of the compound (II) is prepared in a first stage by one of the methods already cited for synthesizing the compound C which is more soluble than the compound (II) in aprotic dipolar solvents. The compound C is then reduced for example by means of a metal hydride or borane as already indicated, in order to obtain the compound D. It is then possible to carry out the desired chemical modification in order to convert the substituent R3 to the substituent R4. If the solubility of the compound (III) is sufficient, it is also possible to directly reduce the carboxylic acid functional group at the 6-position in order to prepare the compound D according to one of the methods already cited. The compound (II) is then prepared from the compound D. This variant is represented in scheme 6.

According to a particular embodiment, the synthesis of 6-hydroxymethyl-3-phenylpyrazolo[3,2-c]-1,2,4-triazole of formula (II) may be carried out directly from 6-carboxy-3-phenylpyrazolo[3,2-c]-1,2,4-triazole (III). It is preferably obtained according to the procedure of scheme 2 which consists in converting beforehand 6-carboxy-3-phenylpyrazolo[3,2-c]-1,2,4-triazole to 6-carboxymethyl-3-phenylpyrazolo[3,2-c]-1,2,4-triazole. The 6-hydroxymethyl-3-phenylpyrazolo[3,2-c]-1,2,4-triazole may also be prepared from 6-carboxy-3-(3',4'-dichloro)phenylpyrazolo[3,2-c]-1,2,4-triazole according to one of schemes 3, 4, 5 or 6.

According to scheme 3, 6-carboxy-3-(3',4'-dichloro)phenylpyrazolo[3,2-c]-1,2,4-triazole is converted to 6-carboxy-3-phenylpyrazolo[3,2-c]-1,2,4-triazole for example by catalytic reduction in the presence of a metal catalyst such as palladium or palladium hydroxide at a hydrogen pressure of 2 to 100 bar, preferably of 2 to 60 bar, at a temperature ranging from 10 to 90° C., preferably between 20 and 60° C. The reaction is preferably carried out in a basic medium containing for example an organic base such as a primary, secondary or tertiary amine, for example triethylamine, ethyldiisopropylamine or butylamine, or an inorganic base such as sodium hydroxide, potassium hydroxide, potassium carbonate, sodium carbonate, potassium hydrogen carbonate, sodium hydrogen carbonate, or a mixture of these bases. The hydrogenation is carried out in a solvent such as an alcohol, such as ethanol or methanol, in water, in an aqueous-alcoholic mixture or in a mixture of water and an aprotic dipolar solvent such as dioxane or THF. Preferably, the reaction is carried out in a water-aprotic dipolar solvent mixture. The 6-carboxy-3-phenylpyrazolo[3,2-c]-1,2,4-triazole is then directly reduced to 6-hydroxymethyl-3-phenylpyrazolo[3,2-c]-1,2,4-triazole (scheme 3) or is first of all esterified to a methyl or ethyl ester before being reduced (scheme 4).

According to scheme 5, 6-carboxy-3-(3',4'-dichloro)phenylpyrazolo[3,2-c]-1,2,4-triazole is first of all esterified to the compound C, the compound C is then reduced in order to form 6-hydroxymethyl-3-(3',4'-dichloro)phenylpyrazolo[3,2-c]-1,2,4-triazole. The conversion of the substituent R3=1-(3',4'-dichloro)phenyl to R4=phenyl is carried out by catalytic hydrogenation under the conditions already described.

According to scheme 6, the carboxyl at the 6-position is first of all reduced to hydroxymethyl and then 6-hydroxymethyl-3-(3',4'-dichloro)phenylpyrazolo[3,2-c]-1,2,4-triazole is converted to 6-hydroxymethyl-3-phenylpyrazolo[3,2-c]-1,2,4-triazole by catalytic reduction under the above-mentioned conditions.

The subject of the invention is finally a colored product which can be obtained by reacting at least one pyrazolo[3,2-c]-1,2,4-triazole coupler of formula (I) or one of its addition salts with an acid or a base as defined above, and at least one oxidation base.

The examples which follow serve to illustrate the invention without however presenting a limiting character.

EXAMPLES

Example 1

Synthesis of 6-hydroxymethyl-3-phenylpyrazolo[3,2-c]-1,2,4-triazole (H) According to Scheme 3

Step 1

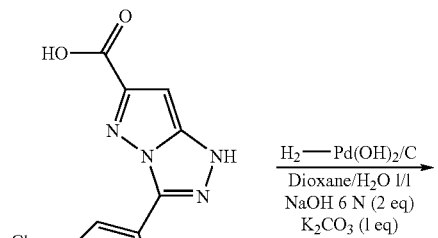

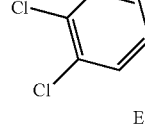

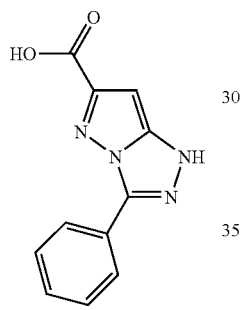

F 60 g of 6-carboxy-3-(3',4'-dichloro)phenylpyrazolo[3,2-c]-1,2,4-triazole E and 28.05 g of potassium carbonate are dissolved in 1.8 liters of a mixture composed of 69 ml of 6 N sodium hydroxide and dioxane at 50% in water. This solution is transferred into a hydrogenator and supplemented with 9 g of 20% Pd(OH)$_2$/C and 50% moisture. The medium is purged twice with nitrogen before introducing 35 bar of hydrogen, and then heated at 35° C. for 8 hours. After eliminating the hydrogen, the medium is filtered. The filtrate is partially concentrated in order to remove the dioxane and the residual aqueous solution is acidified with an aqueous hydrochloric acid solution diluted to a pH equal to 2. The precipitate thus obtained is filtered, drained, washed with distilled water and dried under vacuum. 45 g of compound F are thus obtained in the form of white crystals (yield 97.6%).

Elemental Analysis:

|  | C | H | N | O |
|---|---|---|---|---|
| Calculated | 57.90 | 3.53 | 24.55 | 14.02 |
| Found | 57.30 | 3.47 | 24.35 | 14.38 |

NMR (1H, 400 MHz, DMSO d6): 6.38 (s, 1H), 7.56 (m, 1H), 7.62 (dd, 2H), 8.43 (dd, 2H), 12.98 (bs, 1H), 13.45 (s, 1H).

NMR (13C, 39.5 MHz, DMSO d6): 80.65, 125.37, 125.59, 128.99, 130.10, 137.59, 147.56, 151.05, 163.75

Step 2

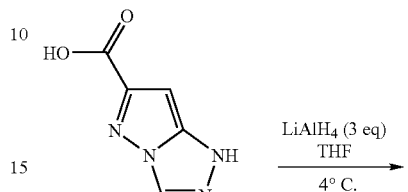

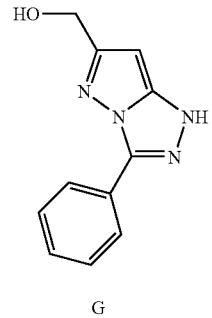

G

Under an inert gas, 1 g of compound F is solubilized in 400 ml of anhydrous THF at room temperature. After cooling to 0° C., 333 mg of LiAlH$_4$ are added in small fractions over 1 hour. The reaction medium becomes opaque and white. The temperature is allowed to rise to room temperature. The reaction is monitored by TLC.

After 3 h 30 min, 0.2 eq LiAlH$_4$ (33 mg) is again added at room temperature and then 1 hour later again 0.4 eq of LiAlH$_4$ (66 mg) and finally after 45 min, another 0.4 eq (66 mg) of LiAlH$_4$ is added and the medium is kept stirred at room temperature. After one night, the reaction is complete.

The reaction medium is acidified to a pH equal to 3 with 1 M HCl and it gradually decolorizes. The medium is then extracted with ethyl acetate. A grayish precipitate appears, and it is filtered on No. 4 sintered glass. The extraction is continued by adding a saturated aqueous NaCl solution. The organic phase is dried over a sodium sulfate, filtered and concentrated to dryness. An orange-colored solid is thus obtained. The latter is washed with Et$_2$O and then AcOEt and filtered on No. 4 sintered glass. A pink-beige powder is thus obtained after drying under vacuum. 360 mg of compound G are thus isolated with a yield of 38.4%.

Elemental Analysis:

|  | C | H | N | O |
|---|---|---|---|---|
| Calculated | 61.67 | 4.71 | 26.15 | 7.47 |
| Found | 60.31 | 4.69 | 25.90 | 8.45 |

Example 2

Synthesis of 6-hydroxymethyl-3-phenylpyrazolo[3,2-c]-1,2,4-triazole (H) According to Scheme 4

Step 1

Step 1 of example 1 is reproduced in order to obtain compound F.

Step 2:

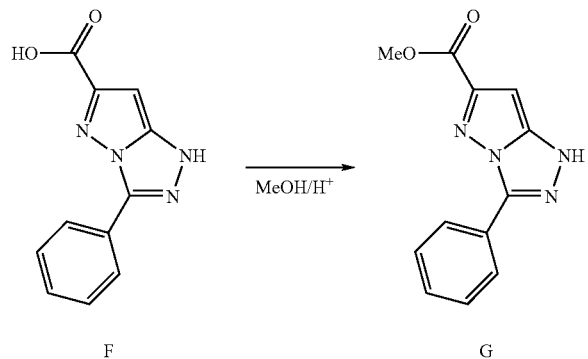

F          G

Under an inert atmosphere, 30 g of compound F are dissolved at room temperature in 6 liters of anhydrous methanol. 3 g of 10-camphor sulfonic acid are added and then the medium is heated under reflux for 48 hours. The medium is allowed to return to room temperature, and compound G precipitates on cooling. The compound G thus formed is filtered, drained and washed several times with ethyl ether before being dried under vacuum. 23.88 g of methyl ester G are thus obtained in the form of a powder with a yield of 75%

Step 3

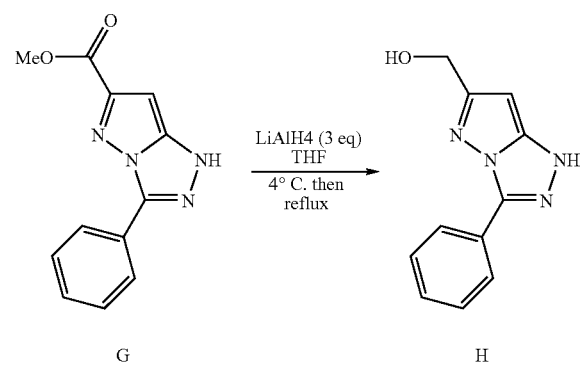

G          H

Under an inert atmosphere, 2.33 liters of anhydrous THF and then 20 grams of ester G are introduced. After stirring for 15 min, the medium is cooled to 0° C. and 10.6 g of LiAlH$_4$ are added in small portions over 30 min while the temperature is kept at 0° C. The medium is then heated under reflux for 4 h 30 min and then left overnight at room temperature. The medium is then again cooled to 0° C. and hydrolyzed. The precipitate obtained is filtered and drained. The filtrate is concentrated under vacuum to a volume of 200 ml before being acidified to a pH equal to 3 with an aqueous solution of dilute hydrochloric acid. The precipitate of compound H thus formed is filtered, drained and dried under vacuum, giving 15.5 g of compound H in the form of a beige powder with a yield of 87.6%.

Examples of Dyeing

Examples 3 to 5

The following dyeing compositions were prepared (content in moles):

| Examples | 3 (Inv) | 4 (Inv) | 5 (Inv) |
|---|---|---|---|
| 6-Hydroxymethyl-3-phenylpyrazolo-[3,2-c]-1,2,4-triazole | $3 \times 10^{-3}$ | $3 \times 10^{-3}$ | $3 \times 10^{-3}$ |
| Para-phenylenediamine | $3 \times 10^{-3}$ | — | — |
| 3,7-Diaminopyrazolo[1,5-a]pyrimidine.2HCl | — | $3 \times 10^{-3}$ | — |
| N,N-bis-(β-hydroxyethyl)-para-phenylenediamine.H$_2$SO$_4$.H$_2$O | — | — | $3 \times 10^{-3}$ |
| Dye carrier (1) | (*) | (*) | (*) |
| Demineralized water qs | 100 g | 100 g | 100 g |

| Dye carrier (1) | |
|---|---|
| Ethyl alcohol at 96° | 18 g |
| Sodium metabisulfite as a 35% aqueous solution | 0.68 g |
| Pentasodium salt of diethylenetriaminopentaacetic acid | 1.1 g |
| Aqueous ammonia at 20% | 10 g |

At the time of use, each composition of examples 3 to 5 is mixed with an equal weight of hydrogen peroxide at 20 volumes (6% by weight).

Each mixture obtained is applied to locks of gray hair which is 90% white, permanently waved (BP) or natural (BN). After leaving in for 30 min, the locks are rinsed, washed with standard shampoo, rinsed again and then dried.

The following dyeing results were obtained.

| | BN | BP |
|---|---|---|
| Example 3 | Slightly ash deep purple | slightly ash deep purple |
| Example 4 | slightly coppery iridescent red | iridescent red |
| Example 5 | violet | intense violet |

Examples 6 and 7

The following dyeing compositions were prepared (contents in moles):

| Examples | 6 (inv) | 7 (comp) |
|---|---|---|
| 6-Hydroxymethyl-3-phenylpyrazolo-[3,2-c]-1,2,4-triazole | $6.4 \times 10^{-3}$ | |
| N,N-bis-(β-hydroxyethyl)-para-phenylenediamine.H$_2$SO$_4$.H$_2$O | $6.4 \times 10^{-3}$ | $6.4 \times 10^{-3}$ |
| 4,6-Dimethyl-2H-pyrazolo[3,2c]-1,2,4-triazole | | $6.4 \times 10^{-3}$ |
| Dye carrier (2) | (*) | (*) |
| Demineralized water qs | 100 g | 100 g |

| Dye carrier (2) | |
|---|---|
| Polyglycerolated oleyl alcohol containing 2 moles of glycerol | 4.0 g |
| Polyglycerolated oleyl alcohol containing 4 moles of glycerol containing 78% of active substances (AS) | 5.69 g AS |
| Oleic acid | 3.0 g |

-continued

| | |
|---|---|
| Oleyl amine containing 2 moles of ethylene oxide sold under the trade name ETHOMEEN O12 by the company AKZO | 7.0 g |
| Diethylaminopropyl laurylaminosuccinamate, sodium salt containing 55% of AS | 3.0 g AS |
| Oleyl alcohol | 5.0 g |
| Diethanolamide of oleic acid | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulfite containing in aqueous solution containing 35% of AS | 0.455 g AS |
| Ammonium acetate | 0.8 g |
| Antioxidant, sequestrant | qs |
| Perfume, preservative | qs |
| Aqueous ammonia containing 20% of $NH_3$ | 10.0 g |

At the time of use, each composition of Examples 6 and 7 is mixed with an equal weight of hydrogen peroxide at 20 volumes (6% by weight).

Each mixture obtained is applied to locks of gray hair which is 90% white, permanently waved (BP) or natural (BN). After leaving in for 30 min, the locks are rinsed, washed with a standard shampoo, rinsed again and then dried.

The color of the locks is evaluated by means of a CM 2002 MINOLTA spectrophotometer. The shades measured on the MINOLTA CM 2002 are calculated as MUNSELL values (ASTM D 1535-68 standard), in which the value H denotes the shade or HUE, the value V denotes the intensity or VALUE, and the value C the purity or CHROMATICITY.

The results are presented in the table below.

| | Natural gray hair | | | Permanently waved gray hair | | |
|---|---|---|---|---|---|---|
| Examples | H | V | C | H | V | C |
| Example 6 | 3.1 P | 3 | 4.2 | 3 P | 2.2 | 4.8 |
| Example 7 | 0.4 R | 4.1 | 2 | 6.4 R P | 3.4 | 2.7 |

These results show that the coupler 6-hydroxymethyl-3-phenylpyrazolo[3,2-c]-1,2,4-triazole makes it possible to obtain more chromatic violet glints.

Examples 8 and 9

Deferred Application

The following compositions were prepared (moles)

| Examples | 8 | 9 |
|---|---|---|
| 6-Hydroxymethyl-3-phenylpyrazolo-[3,2-c]-1,2,4-triazole | 3 × 10⁻³ | — |
| 4,6-Dimethyl-2H-pyrazolo[3,2c]-1,2,4-triazole (comp) | — | 3 × 10⁻³ |
| N,N-bis-(β-hydroxyethyl)-para-phenylenediamine.$H_2SO_4$.$H_2O$ | 3 × 10⁻³ | 3 × 10⁻³ |
| Dye carrier (3) | (*) | (*) |
| Demineralized water qs | 100 g | 100 g |

Dye carrier (3)

| | |
|---|---|
| Ethyl alcohol at 96° | 18 g |
| Sodium metabisulfite as a 35% aqueous solution | 0.68 g |
| Pentasodium salt of diethylenetriaminopentaacetic acid | 1.1 g |
| Aqueous ammonia at 20% | 10 g |

The compositions of examples 8 to 9 are mixed with an equal weight of hydrogen peroxide at 20 volumes (6% by weight). A portion of each of the compositions is applied to locks of gray hair which is 90% natural gray hair (BN) or permanently waved gray hair (BP) at the time of the mixing (T0), a second portion is applied to new locks 15 min after the mixing (T15) and a third portion is applied 30 minutes after the mixing (T30). The application to the locks is carried out according to the procedure described above.

The following results were obtained.

| | | COUPLING POWER | 90% BN glints | 90% BP glints |
|---|---|---|---|---|
| Example 9 | T0 | 4 | intense violet iridescent | intense slightly iridescent violet |
| | T15 | 3.5 | violet iridescent | intense slightly iridescent violet |
| | T30 | 3 | slightly violet slightly ash iridescent | slightly iridescent violet |
| Example 8 | T0 | 4 | very slightly iridescent bluish violet | Intense bluish violet |
| | T15 | 4 | ash very slightly iridescent bluish violet | very slightly ash bluish violet |
| | T30 | 4 | iridescent very slightly ash bluish violet | very slightly ash bluish violet |

The coupling power corresponds to the classification of natural shades (see "Science des Traitements Capillaires" by C. ZVIAK, Ed. Masson 1988, p. 278). A power of 3 corresponds to a dark chestnut 5 brown, a power of 4 corresponds to a chestnut brown.

These results show that the coupler 6-hydroxymethyl-3-phenylpyrazolo[3,2-c]-1,2,4-triazole exhibits, in deferred application, a lesser variation of the coloration.

The invention claimed is:

1. A composition for dyeing keratinous fibers comprising, in a medium appropriate for dyeing,
at least one compound chosen from a pyrazolo[3,2-c]-1,2,4-triazole of formula (I) and the acid addition salts and base addition salts thereof:

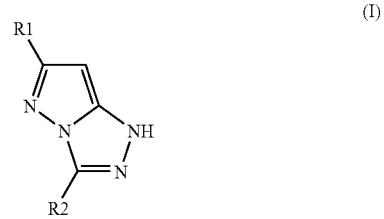

wherein

R1 is hydroxymethyl, and

R2 is an aryl group optionally substituted with at least one radical chosen from halogen, nitro, cyano, alkyl, hydroxyl, alkoxy, amino, alkylamino, dialkylamino, acylamino, sulfonamido, alkylthio, alkoxycarbonyl, carboxy, and sulfo radicals; and at least one oxidation base.

2. The composition according to claim 1 wherein the keratinous fibers are human keratinous fibers.

3. The composition according to claim 2, wherein the human keratinous fibers are hair.

4. The composition according to claim 1, wherein R2 is a phenyl group optionally substituted with 1 to 3 radicals.

5. The composition according to claim 1, wherein the at least one coupler is present in the composition in an amount ranging from 0.001% to 10% by weight relative to the total weight of the composition.

6. The composition according to claim 5, wherein the at least one coupler is present in the composition in an amount ranging from 0.005% to 6% by weight relative to the total weight of the composition.

7. The composition according to claim 1, wherein the at least one oxidation base is chosen from para-phenylenediamines, bis-phenylalkylenediamines, para-aminophenols, ortho-aminophenols, heterocyclic bases, and the acid addition salts thereof.

8. The composition according to claim 1, wherein the at least one oxidation base is present in the composition in an amount ranging from 0.001% to 10% by weight relative to the total weight of the composition.

9. The composition according to claim 8, wherein the at least one oxidation base is present in the composition in an amount ranging from 0.005% to 6% by weight relative to the total weight of the composition.

10. The composition according to claim 1, further comprising a direct dye.

11. A method for the oxidation dyeing of keratinous fibers, comprising applying at least one dyeing composition comprising a compound chosen from a pyrazolo[3,2-c]-1,2,4-triazole of formula (I) and the acid addition salts and base addition salts thereof:

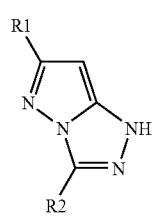

wherein

R1 is hydroxymethyl, and

R2 is an aryl group optionally substituted with at least one radical chosen from halogen, nitro, cyano, alkyl, hydroxyl, alkoxy, amino, alkylamino, dialkylamino, acylamino, sulfonamido, alkylthio, alkoxycarbonyl, carboxy, and sulfo radicalsis applied to the keratinous fibers; and developing color with at least one oxidizing agent.

12. The method according to claim 11, wherein the keratinous fibers are human keratinous fibers.

13. The method according to claim 12, wherein the human keratinous fibers are hair.

14. The method according to claim 11, wherein the oxidizing agent is chosen from hydrogen peroxide, urea peroxide, alkali metal bromates, persalts, peracids, and oxidase enzymes.

15. The method according to claim 14, wherein the persalts are chosen from perborates and persulfates.

16. A method for the oxidation dyeing of keratinous fibers according to claim 11, wherein at least one at least one oxidizing agent is mixed at the time of application with the dyeing composition.

17. A method for the oxidation dyeing of keratinous fibers according to claim 11, wherein the at least one oxidizing agent is applied in the form of an oxidizing composition simultaneously with or sequentially to the dyeing composition.

18. A multicompartment dyeing kit, comprising a first compartment comprising a compound chosen from a pyrazolo[3,2-c]-1,2,4-triazole of formula (I) and the acid addition salts and base addition salts thereof:

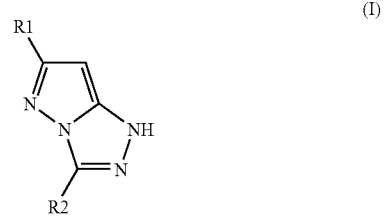

wherein

R1 is hydroxymethyl, and

R2 is an aryl group optionally substituted with at least one radical chosen from halogen, nitro, cyano, alkyl, hydroxyl, alkoxy, amino, alkylamino, dialkylamino, acylamino, sulfonamido, alkylthio, alkoxycarbonyl, carboxy, and sulfo radicals; and a second compartment comprising an oxidizing composition.

19. A colored product obtained by reacting at least one compound chosen from a pyrazolo[3,2-c]-1,2,4-triazole of formula (I) and the acid addition salts and base addition salts thereof:

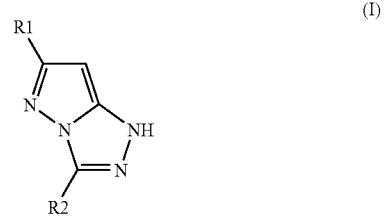

wherein

R1 is hydroxymethyl, and

R2 is an aryl group optionally substituted with at least one radical chosen from halogen, nitro, cyano, alkyl, hydroxyl, alkoxy, amino, alkylamino, dialkylamino, acylamino, sulfonamido, alkylthio, alkoxycarbonyl, carboxy, and sulfo radicals; and at least one oxidation base.

20. The composition according to claim 1, wherein the pyrazolo[3,2-c]-1,2,4-triazole of formula (I) is chosen from:

6-hydroxymethyl-3-phenylpryazolo[3,2-c]-1,2,4-triazole, 6-hydroxymethyl-3-(p-toluyl)pyrazolo[3,2-c]-1,2,4-triazole, 6-hydroxymethyl-3-(o-toluyl)pryazolo[3,2-c]-1,2,4-triazole, 6-hydroxymethyl-3-(m-toluyl)pryazolo[3,2-c]-1,2,4-triazole, 6-hydroxymethyl-3-(3-hydroxyphenyl)pyrazolo[3,2-c]-1,2,4-triazole, 6-hydroxymethyl-3-(4-hydroxyphenyl)pyrazolo[3,2-c]-1,2,4-triazole, 6-hydroxymethyl-3-(3-aminophenyl)pyrazolo[3,2-c]-1,2,4-triazole, 6hydroxymethyl-3-(4-aminophenyl)pyrazolo[3,2-c]-1,2,4-triazole, and the acid addition salts and base addition salts thereof.

21. A composition for dyeing keratinous fibers comprising, in a medium appropriate for dyeing, a first composition comprising at least one compound chosen from a pyrazolo[3,2-c]-1,2,4-triazole of formula (I) and the acid addition salts and base addition salts thereof:

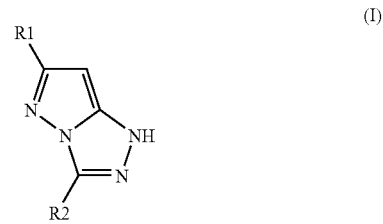

(I)

wherein

R1 is hydroxymethyl, and

R2 is an aryl group optionally substituted with at least one radical chosen from halogen, nitro, cyano, alkyl, hydroxyl, alkoxy, amino, alkylamino, dialkylamino, acylamino, sulfonamido, alkylthio, alkoxycarbonyl, carboxy, and sulfo radicals; and at least one oxidation base; and a second composition comprising at least one oxidation agent; wherein, when the first and second compositions are mixed and applied to keratinous fibers, decreased variance in the coloration of the keratinous fibers results whether the composition is applied at the time the first and second compositions are mixed or whether the composition is applied at a deferred time subsequent to mixing.

* * * * *

UNITED STATES PATENT AND TRADEMARK OFFICE
CERTIFICATE OF CORRECTION

PATENT NO.         : 7,192,452 B2                                    Page 1 of 1
APPLICATION NO. : 10/467818
DATED              : March 20, 2007
INVENTOR(S)        : Laurent Vidal and Sylvie Genard It is certified that error appears in the above-identified patent and that said Letters Patent is hereby corrected as shown below:

In claim 11, column 19, lines 42-43, "pyrazolo[3,2-c]-1,2,4-triazole" should read --pyrazolo[3,2-c]-1,2,4-triazole--.

In claim 19, column 20, line 45, "pyrazolo[3,2-c]-1,2,4-triazole" should read --pyrazolo[3,2-c]-1,2,4-triazole--.

In claim 20, column 21, line 3, "6-hydroxymethyl-3-phenylpryazolo[3,2-c]-1,2,4-triazole," should read --6-hydroxymethyl-3-phenylpyrazolo[3,2-c]-1,2,4-triazole,--.

In claim 20, column 21, lines 7-8, "6-hydroxymethyl-3-(o-toluyl)pryazolo[3,2-c]-1,2,4-triazole," should read --6-hydroxymethyl-3-(o-toluyl)pyrazolo[3,2-c]-1,2,4-triazole,--.

In claim 20, column 21, lines 10-11, "6-hydroxymethyl-3-(m-toluyl)pryazolo[3,2-c]-1,2,4-triazole," should read --6-hydroxymethyl-3-(m-toluyl)pyrazolo[3,2-c]-1,2,4-triazole,--.

In claim 20, column 21, lines 19-20, "6hydroxymethyl-3-(4-aminophenyl)pyrazolo[3,2-c]-1,2,4-triazole," should read --6-hydroxymethyl-3-(4-aminophenyl)pyrazolo[3,2-c]-1,2,4-triazole,--.

Signed and Sealed this

Twenty-second Day of May, 2007

JON W. DUDAS
*Director of the United States Patent and Trademark Office*